US006692955B1

(12) United States Patent
Meredith et al.

(10) Patent No.: US 6,692,955 B1
(45) Date of Patent: Feb. 17, 2004

(54) HIV VACCINE

(75) Inventors: David Mark Meredith, Leeds (GB); Alexander Fred Markham, Leeds (GB)

(73) Assignee: University of Leeds, Leeds (GB)

( * ) Notice: Subject to any disclaimer, the term of this patent is extended or adjusted under 35 U.S.C. 154(b) by 0 days.

(21) Appl. No.: 09/856,652

(22) PCT Filed: Nov. 25, 1999

(86) PCT No.: PCT/GB99/03923

§ 371 (c)(1), (2), (4) Date: Jul. 16, 2001

(87) PCT Pub. No.: WO00/32802

PCT Pub. Date: Jun. 8, 2000

(30) Foreign Application Priority Data

Nov. 28, 1998 (GB) .............................................. 9826069

(51) Int. Cl.[7] .......................... C12N 15/74; C12N 5/02; C12N 15/09; A61K 31/70

(52) U.S. Cl. .................... 435/320.1; 435/325; 435/455; 514/44

(58) Field of Search .............................. 435/320.1, 325, 435/455; 514/44

(56) References Cited

U.S. PATENT DOCUMENTS 5,670,352 A * 9/1997 Biesinger-Zwosta et al. .... 435/456

FOREIGN PATENT DOCUMENTS

WO WO98/10083 3/1998
WO WO 9810083 A1 * 3/1998 ........... C12N/15/86

OTHER PUBLICATIONS

Wrin et al, J Virol, 1995;69:39–48.*
Natuk et al, PNAS 1992;89:7777–81.*
McMichael et al, Bri Med Bul 2002;62:87–98.*
Kumar et al, J Immunol Methods 1999 Nov 19;230:47–58.*
Perales et al, J Acquir Immune Defic Syndr Hum Retroviral 1995;10:27–35.*
Eck et al, Phar Basis Ther 1995; 77–101.*
Mustafa et al, J Virol. 1997;229:269–78.*
E.A. Frovola–Jones, et al. "Evaluation of Herpesvirus Saimiri–Based Gene Delivery Into Human Hematopoietic and Stromal Progenitors." vol. 92, No. 10, Nov. 15, 1998, Abstract No. 4619.
Igor M. Belyakov, et al. "Induction of a Mucosal Cytotoxic T–Lymphocyte Response by Intrarectal Immunization with a Replication–Deficient Recombinant Vaccinia Virus Expressing Human Immunodeficiency Virus 89.6 Envelope Protein." *Journal of Virology*, vol. 72, No. 10, Oct. 1998, pp. 8264–8272.
J. Scott Cairns and Nava Sarver. "Mini–Review: New Viral Vectors for HIV Vaccine Delivery." *AIDS Research and Human Retroviruses*. vol. 14, No. 17, 1998, pp. 1501–1508.
Joanne C. Griffiths, et al. "Induction of High–Titer Neutralizing Antibodies Using Hybrid Human Immunodeficiency Virus V3–Ty Viruslike Particles in a Clinically Relevant Adjuvant." *Journal of Virology*, vol. 65, No. 1, Jan. 1991, pp. 450–456.

* cited by examiner

*Primary Examiner*—Anne M. Wehbe'
*Assistant Examiner*—Q. J. Li
(74) *Attorney, Agent, or Firm*—Myers Bigel Sibley & Sajovec, P.A.

(57) ABSTRACT

A herpesvirus saimiri (HVS) vector which has inserted therein at least a part of a gene encoding an envelope protein of HIV for use in delivering said protein to a specific cell population such as T cell lymphocytes and/or macrophages. The invention also provides a vaccine comprising the recombinant vector.

16 Claims, 1 Drawing Sheet

SEQUENCE LISTING

<160> NUMBER OF SEQ ID NOS: 10

<210> SEQ ID NO 1
<211> LENGTH: 18
<212> TYPE: DNA
<213> ORGANISM: Unknown Organism
<220> FEATURE:
<223> OTHER INFORMATION: Description of Unknown Organism:VIRAL PRIMER /
      LINKER

<400> SEQUENCE: 1
tgaattcgga tccgcatg                                                 18

<210> SEQ ID NO 2
<211> LENGTH: 18
<212> TYPE: DNA
<213> ORGANISM: Unknown Organism
<220> FEATURE:
<223> OTHER INFORMATION: Description of Unknown Organism:VIRAL PRIMER/
      LINKER

<400> SEQUENCE: 2
cgcgacttaa gcctaggc                                                 18

<210> SEQ ID NO 3
<211> LENGTH: 34
<212> TYPE: DNA
<213> ORGANISM: Unknown Organism
<220> FEATURE:
<223> OTHER INFORMATION: Description of Unknown Organism:VIRAL PRIMER /
      LINKER

<400> SEQUENCE: 3
aattcatggc aacgaagaca gcgcaaccta gcgc                               34

<210> SEQ ID NO 4
<211> LENGTH: 26
<212> TYPE: DNA
<213> ORGANISM: Unknown Organism
<220> FEATURE:
<223> OTHER INFORMATION: Description of Unknown Organism:VIRAL PRIMER /
      LINKER

<400> SEQUENCE: 4
gtaccgttgc ttctgtcgcg ttggat                                        26

<210> SEQ ID NO 5
<211> LENGTH: 34
<212> TYPE: DNA
<213> ORGANISM: Unknown Organism
<220> FEATURE:
<223> OTHER INFORMATION: Description of Unknown Organism:VIRAL PRIMER /
      LINKER

<400> SEQUENCE: 5
aacgaattcg gatccttaat aataatgagc tgta                               34

<210> SEQ ID NO 6
<211> LENGTH: 34
<212> TYPE: DNA
<213> ORGANISM: Unknown Organism
<220> FEATURE:
<223> OTHER INFORMATION: Description of Unknown Organism:VIRAL PRIMER /
      LINKER

<400> SEQUENCE: 6

-continued

```
ttgcttaagc ctaggaatta ttattactcg acat                        34

<210> SEQ ID NO 7
<211> LENGTH: 32
<212> TYPE: DNA
<213> ORGANISM: Unknown Organism
<220> FEATURE:
<223> OTHER INFORMATION: Description of Unknown Organism:VIRAL PRIMER /
      LINKER

<400> SEQUENCE: 7
ggcgaattcg tctataactg actgggttgc tg                          32

<210> SEQ ID NO 8
<211> LENGTH: 32
<212> TYPE: DNA
<213> ORGANISM: Unknown Organism
<220> FEATURE:
<223> OTHER INFORMATION: Description of Unknown Organism:VIRAL PRIMER /
      LINKER

<400> SEQUENCE: 8
gccctgcagg cagttactca ccatagcttg ag                          32

<210> SEQ ID NO 9
<211> LENGTH: 33
<212> TYPE: DNA
<213> ORGANISM: Unknown Organism
<220> FEATURE:
<223> OTHER INFORMATION: Description of Unknown Organism:VIRAL PRIMER /
      LINKER

<400> SEQUENCE: 9
gccctgcagc aagtgtccaa gctctacttg tgc                         33

<210> SEQ ID NO 10
<211> LENGTH: 34
<212> TYPE: DNA
<213> ORGANISM: Unknown Organism
<220> FEATURE:
<223> OTHER INFORMATION: Description of Unknown Organism:VIRAL PRIMER /
      LINKER

<400> SEQUENCE: 10
ggggcatccc tattgatgtg ccaagcaata gggt                        34
```

HIV VACCINE

RELATED APPLICATION INFORMATION

Figure 1A:

This application claims priority under 35 U.S.C. § 371 from PCT Application No. PCT/GB99/03923 (published under PCT Article 21(2) in English), filed on Nov. 25, 1999, which claims the benefit of Great Britain Application Serial No. 9826069.8, filed on Nov. 28, 1998, the disclosures of which are incorporated by reference herein in their entireties.

The invention relates to a method of virus manipulation; means therefor and products thereof which have particular, but not exclusive, application in gene therapy/vaccine development.

A virus-derived vector capable of efficient gene delivery to human T lymphocytes would have a wide range of uses in human gene therapy. An obvious disease target would be human immunodeficiency virus (HIV) infection, where such a vector could have use both in the prevention and therapy of infection. Two virus vector systems which do not cause a cytopathic effect in vitro, retroviruses and adeno-associated virus, both target dividing cells only, and are thus inappropriate for use with a CD4 T cell population which are mainly non-dividing.

Virus based gene therapy systems currently in clinical trial or in development include vectors based on adenoviruses, retroviruses and human herpesviruses (1, 2, 3). All these systems have inherent disadvantages. Adenovirus vectors have constraints on the size of heterologous DNA incorporated, can cause toxic side effects and induce a vigorous immune response resulting in rapid clearance of infected and therefore gene targeted cells (4, 5). A major drawback in retroviral systems based on murine leukemia viruses is their inability to infect non-dividing cells. Thus cells must be removed, activated, infected in vitro, and then delivered back to the patient. A further disadvantage is the high inherent mutation rate caused by reverse transcription (6).

Herpesvirus vector systems offer the potential of delivering >50 kb of heterologous DNA, the infection of non-dividing cells and maintenance of their genome episomally in a non-replicative form (7). However, nearly all vector systems in development to date are based on herpes simplex virus and are likely to be ineffective in many individuals due to an immune response present in >80% of the population, already induced by the wild type virus (8). A herpesvirus of non-human origin, capable of infecting human cells, therefore represents an attractive candidate as a gene therapy vector, as there will be no innate immune response in the recipient to prevent infection in vitro.

Figure 1B:

Herpesvirus saimiri (HVS) is a lymphotropic rhadinovirus ($\gamma$2 herpesvirus) of squirrel monkeys (*Saimiri sciureus*). The virus genome may be detected in an episomal form in T cells and causes no apparent disease in the natural host. Whereas type A and B strains similarly do not cause apparent disease in other monkey species, C type strains of this virus are oncogenic in certain New World primates (9). C strains also have the ability to transform human T cells in vitro. The gene product responsible for cell transformation has been identified as the STP gene (ORF1) (10). STP is non-essential for virus replication in vitro and in vivo; natural deletion mutants exist in C strains which are non-oncogenic. Therefore a virus of strain A, which has the STP gene deleted is unable to transform any type of cell. Virus strains lacking this gene and carrying several heterologous genes have been constructed and studies carried out in vitro have demonstrated high efficiency and long term expression of the heterologous gene product (11). The virus DNA remains episomal with no detectable expression of virus genes, but with stable heterologous expression in the absence of selection. Furthermore, the virus genome segregates efficiently between dividing cells, presumably in a manner similar to the human $\gamma$2 herpesvirus, Epstein-Barr Virus. Advantageously, HVS which naturally infects non-human primates has also been found to infect human T lymphocytes. As previously mentioned, this feature of HVS can be used to advantage for providing in man a wide range of gene therapies. For example, it is of note that a major target cell type for HIV infection in man is T lymphocytes. We therefore speculated that the expression of HIV protein in the correct oligomeric configuration in vivo on the surface of a T lymphocyte should induce an effective humoral and cellular anti-HIV immune response. HVS can be used to advantage in the delivery of a gene encoding large HIV proteins because, as previously mentioned, it has the potential of delivering >50 kb of heterologous DNA and is further capable of infecting T lymphocytes.

In our studies we chose an envelope gene from a primary isolate of HIV as the gene to be delivered by HVS for the development of the potential vaccine.

Studies have shown that immunogens based on the envelope protein or defined epitopes thereof induce both virus neutralizing antibodies and HIV-specific cytotoxic T lymphocytes (12, 13, 14, 15). Furthermore, chimpanzees have been successfully protected against HIV challenge, with protection correlated with the presence of high titre neutralizing antibodies (12). However, recent studies have shown that antibodies raised against these immunogens encoding envelope sequences from laboratory adapted isolates are ineffective at neutralizing primary isolates from HIV infected individuals (16). Envelope proteins from primary isolates confer different characteristics to the virus as compared to laboratory adapted isolates. These include the ability to infect macrophages and the inability to induce syncytia, the cytopathic effect seen with laboratory adapted isolates. Furthermore, anti-envelope antibodies from HIV positive individuals show cross isolate neutralizing ability (17, 18). Analysis of HIV neutralizing antibodies have also suggested that the envelope immunogen must be presented in the authentic, oligomeric, non-denatured form to induce heterologous neutralizing antibodies (15, 19). Recent reports also indicate the need to elicit a polyclonal antibody response as human monoclonal antibodies isolated from patients fail to neutralize certain primary isolates (18, 20). Further evidence for the feasibility of a vaccine strategy utilizing a primary macrophage-tropic envelope is provided by a study using the simian immunodeficiency model (SIV) model (21). Macaques immunized with an attenuated macrophage-tropic SIV developed cross-neutralizing antibodies and were successfully protected against heterologous isolate challenge.

The studies outlined above indicate that the induction of a vigorous immune response against the HIV envelope protein may protect against virus challenge or constrain the virus if infection does occur. Long term survivors who remain health); 12–15 years after infection have high levels of neutralizing antibodies (17). Delivery of a primary isolate envelope gene by a virus based vector to the correct cell population offers the potential to induce an effective anti-HIV cross-isolate immune response, an essential requirement of any candidate HIV vaccine. This gene therapy approach may also have therapeutic value to individuals who have progressed to AIDS. It has been shown that expression of envelope protein in T cells induces partial resistance to infection, and significantly induces total resistance to cytopathic effects (22). T cells infected with the recombinant HVS may therefore be protected in vivo.

We believe that vectors derived from HVS offer a wide range of opportunities to target both protective and therapeutic genes to human T cells, offering the unique opportunity to deliver a stably-expressing, extrachromosmal element, to a non-dividing cell population. Moreover we have demonstrated efficient infection of the T-cell line Jurkat, by a recombinant HVS vector expressing HIV gp160.

It is therefore a first object of the invention to provide a gene delivery system/vaccine to deliver at least a part of at least one preselected gene to a specific cell population in which the encoded heterologous protein is presented as an antigen.

In its broadest aspect the invention concerns the use of HVS to deliver heterologous genetic material to a specific cell population and ideally to T lymphocytes and/or macrophages.

According to a first aspect of the invention there is therefore provided a herpesvirus saimiri vector which has inserted therein at least a part of a gene encoding an envelope protein of HIV for use in delivering said protein to a specific cell population.

Preferably, the gene encoding an envelope protein of HIV is from a primary isolate of HIV.

Preferably, the specific cell population is T lymphocytes and/or macrophages.

In yet a further preferred embodiment of the invention said HVS lacks or has a mutation in its STP gene (ORF1) such that the gene product is lacking or is non-functional.

HVS may be suitably modified in order to facilitate its use as an agent for effecting gene transfer. For example, non-essential genes may be deleted in order to facilitate the delivery of large amounts of heterologous DNA, that is in the order of >50 kb. In addition, or alternatively HVS may be modified so as to render it safe and controllable, for example, genes encoding transcriptional control proteins may be mutated and/or deleted so as to disable the replication cycle of the virus.

In our co-pending application, UK patent application no. 9521711.3 we have described in detail the way in which HVS can be modified to advantage to provide for a suitable gene delivery agent and we now incorporate herein by way of reference the content of this co-pending application on the understanding that features of this co-pending application may be used in combination with any features described herein and may be claimed in combination with any one or more feature described herein.

Thus in a further preferred embodiment of the invention there is provided said HVS, as described above, modified in accordance with any one or more of the features described in UK patent application no. 9521711.3.

Ideally, said HVS is modified so that the genes related to ORF4 and/or ORF15 are mutated and/or deleted. This action is favoured because these genes encode glycoproteins that are thought to down-regulate complement activity and thus they may have an affect which is prejudicial to the success of our delivery system/vaccine.

It will be apparent to those skilled in the art that the nature of the heterologous DNA will be determined having regard to the nature of the protein to be introduced into the specific cell population. Where the specific cell population is a T lymphocyte population and/or macrophages it is advantageous to use heterologous DNA encoding at least a part of a protein which when expressed is presented on the surface of a T lymphocyte and/or macrophage. Thus it is preferred to use heterologous DNA encoding at least a part of an envelope, membrane binding protein or the like. The presentation of such protein on the surface of a T lymphocyte should induce an effective humoral and cellular anti-protein immune response.

Further, the nature of heterologous DNA to be provided in said HVS will be such that the corresponding protein fragment or product is sufficient to produce an acceptable or effective response when expressed in, or on the surface of, a specific cell population.

According to a further aspect of the invention there is provided a target cell including said HVS of the invention.

According to a yet further aspect of the invention there is provided a cell transduced with the HVS of the invention.

According to a yet further aspect of the invention there is provided a vector adapted to introduce heterologous DNA encoding at least a part of an HIV protein to be delivered to a specific, which vector is adapted to insert said heterologous DNA into HVS.

According to a yet further aspect of the invention there is provided a method of delivering selected HIV heterologous genetic material to a specific cell population comprising exposing at least a target cell population to herpesvirus saimiri which includes said preselected HIV heterologous material under conditions which favour infection of said population with said virus.

In yet a further embodiment of the invention there is provided a vaccine comprising said HVS and any other suitable excipient or canier. For example, the vaccine may be in the form of a fluid which may be injected intravenously, intramuscularly or subcutaneously into an individual to be vaccinated. Alternatively, said vaccine may be in the form of a fluid which is adapted for use as an aerosol whereby droplets of the vaccine can be delivered to the respiratory tract of an individual to be vaccinated.

Other conventional means of vaccine delivery may be employed in the working of the invention and will be well known to those skilled in the art.

According to a yet further aspect of the invention there is provided use of a vaccine as herein before described for the prophylaxis or treatment of HIV.

The present invention also provides a method of preventing and/or treating an individual likely to contract or suffering from HIV infection, comprising administering a therapeutically effective amount of the vaccine as herein before described.

Preferably, administration of the vaccine may be repeated at selected time intervals.

According to a yet further aspect of the invention the is provided a pharmaceutical comprising a herpesvirus saimiri vector which has inserted therein at least a part of a gene encoding an envelope protein of HIV and optionally further including any of the preferred features hereinbefore described.

According to a yet further aspect of the invention the is provided use of a herpesvirus saimiri vector which has inserted therein at least a part of a gene encoding an envelope protein of HIV in the manufacture of a medicament for use in preventing and/or treating an individual likely to contract or suffering from HIV infection and optionally further including any of the preferred features hereinbefore described.

An embodiment of the invention will now be described by way of example only with reference to the following Figure and materials and methods wherein:

FIGS. 1A and 1B represents phase contrast and blue light microscopy of transduced Jurkat T-cells that express HIV gp160/EGFP phenotype.

Experimental Approach

Tissue culture systems have been developed to produce high titre stocks of HVS. HVS has a lytic life cycle in OMK and Vero cells producing virus plaques which facilitate virus purification (23). A region for insertion of heterologous genes has already been identified between the unique coding region and the start of the repeat sequences in the genome (24). Recombinant viruses incorporating these heterologous genes have been made at high frequency by standard homologous recombination.

Herpesvirus saimiri naturally infects non-human primates and therefore represents an ideal virus candidate for gene therapy both with regards to safety and utility, as humans will not be immunologically primed for this virus. However to minimise any risk of pathogenicity to humans a vector system was developed where a replication deficient virus was produced from a disabled genome. Helper cell lines were produced to enable production of the replication deficient virus carrying the heterologous anti-HIV gene. See UK Patent Application No. 9521711.3

A vector (24), designated pWD11 contains 9 kb of the 3' HVS L-DNA including the L-H junction. The 2.8 kb 3' fragment of this DNA was excised as an EcoRV-SmaI fragment and inserted into a unique NarI site, by blunt-end ligation, upstream of the CMV promoter in the expression vector, pSA91. This vector also contains a polylinker cloning region to enable any heterologous gene of interest to be inserted. The vector is designated pMSL 110. The β-galactosidase gene was inserted into the polylinker cloning region. The resulting vector is designated pMSL 111. This vector has been co-transfected into OMK cells with virus DNA and a virus isolated which expresses β-galactosidase. This virus was used to generate new recombinant viruses where purification was rapidly achieved using blue/white selection of virus plaques.

Analysis of HVS Recombinant Virus Carrying the HIV Envelope Gene

The initial vector system utilized the STP deletion mutant of prototype A strain 11. First generation recombinants carrying the HIV envelope gene were generated using the identified insertion site for heterologous genes (24). Primary isolate envelope clones are available from the MRC AIDS reagent programme and suitable examples were selected. The envelope gene is driven from the CMV IE promoter and contains an heterologous signal sequence. This is because previous work has shown that HIV envelope expression is dependent on the presence of an HIV regulatory gene product, Rev. However changing the signal sequence removes this requirement and relatively high levels of expression have been achieved using the tissue plasminogen activator (t-PA) signal sequence (25). Replacement of the signal sequence is easily achieved due to a unique, conserved, KpnI site located 36 bp from the 5-start of the HIV gp160 coding sequence. The sequence encoding the t-PA signal sequence is 190 bp, therefore synthetic oligomers can be made that encode this and the correct cleavage site between the signal sequence and HIV gp160.

Expression of the envelope protein in cells infected with the recombinant virus was confirmed using inactivated antisera from HIV infected individuals that contain antibodies to primary isolates, available from the MRC AIDS directed programme. Immunofluorescence determined the correct cellular localisation.

Western blots were used to confirm the correct predicted molecular weight and processing of the envelope precursor, gp160, to the surface protein gp120 and the transmembrane protein gp41. These envelope proteins exist as a tetramer in the authentic form (26). Therefore density gradient analysis to confirm the oligomerisation was carried out.

A major role of the HIV envelope protein gp120 is to bind the CD4 cellular receptor. Functionality of the envelope was therefore determined using a CD4 binding immunofluoresence binding assay on infected cells. This in an adaptation of a standard fixed cell immunofluoresence assay, where transfected cells are incubated with soluble CD4, and bound CD4 detected with an anti- CD4-FITC conjugated antibody. Infection of T cell lines which are permissive for HIV by the HVS vector was tested, as well as freshly prepared human peripheral blood lymphocytes. These cells were closely monitored for any evidence of cytopathic effects due to infection. To demonstrate the lack of replication by HVS in these cell lines RT-PCR analysis was carried out to detect immediate-early genes such as ORF 14 and late genes such as ORF 72 using OMK infected cells as a positive control. RNA transcripts from the HVS genoine were detected in the OMK cells but not in the T-cell lines.

Gp160 Expression Cassette

In order to express gp160 clones the t-PA leader sequence was cloned into the polylinker of pMSL110. Synthetic oligomers coding for the t-PA leader were inserted using the SmaI-KpnI restriction sites. The resulting vector is designated pMSL112.

Cloning of Gp160 Clones Into pMSL112

Representative clones of HIV clades A, B, C and E are available from the MRC AIDS Reagent project. These envelope genes have been cloned by PCR into the vector pCRII. Common to all envelope genes is a KpnI restriction site at the HIV gp160 signal sequence cleavage site. In addition there is a KpnI site in the vector pCRII 3' to the gp160 gene. Therefore cassettes encoding the gp160 but lacking the gp160 signal sequence were excised as a KpnI fragment and inserted into the KpnI site of pMSL112. The resulting recombinant vectors contain HVS3' sequence-CMV promoter t-PA leader-gp160 gene. The vectors containing the A, B, C and E clones are designated pMCL113, pMSL114, pMSL115 and pMSL116 respectively. (HIV isolates are divided into genetic clades, currently A-I inclusive: the ones that were used, as described above are examples. It will be appreciated that the vaccine may have to contain envelope genes from a variety of clades, depending on the immune response that is generated.)

To determine the immunogenic potential of the recombinant virus, rabbits were infected. Rabbits are permissive to HVS infection (27) and although they are non-permissive for HIV infection, elicit the production of anti-HIV neutralizing antibodies to envelope immunogens (13). Antisera was analysed to identify which epitopes of the envelope were recognised as compared to the antibodies present in antisera from HIV infected individuals. Purified gp120 (available from MRC AIDS reagent programme) was used in both native and denatured from as an antigen source for direct and competition ELISA tests. Competition ELISA utilised monoclonal antibodies specific for important conformational epitopes: human sera from HIV-infected individuals were also used. Longevity and the induction of memory of the immune response in the infected rabbits were also analysed.

Demonstration of Efficient Infection of the T-cell Line Jurkat by a Recombinant HVS Vector Expressing HIV gp160

A technique was developed for the delivery of HIV gp160 and appropriate marker genes to a T-cell population, using a recombinant HVS vector.

Construction of a Recombinant HVS Expressing an HIV gp160 Enhanced Green Fluorescent Protein (EGFP) Fusion Protein and the Neomycin Resistance (Neo) Gene.

pMSLp160EGFPNeo was constructed by inserting 1.8 kb of HVSA11 sequence from the 3' end of the genome, along with the CMVIE promoter driving expression of the gp160 protein, into the HindIII site of the pEGFP-1 vector (Clontech, Palo Alto, USA). This plasmid was inserted into the HVS genore at a site spanning the junction between the unique and the repeat regions, via a single crossover event in the 3' 1.8 kb unique region of the HVS genome. This was achieved by transfecting Owl Monkey Kidney (OMK)-637 cells (ECACC, Salisbury, UK) with the plasmid, infecting with HVS S4 at a multiplicity of infection (moi) of 1, 24 h later, and harvesting virus which grew in medium containing 600 µg/ml geneticin (Gibco, Paisley, UK). EGFP expression was driven by read through from the CMV promoter upstream of HIV gp160 and green plaques were then isolated and subjected to two further rounds of plaque purification. To check for correct recombination, DNA from recombinant and wild type viruses was isolated by proteinase K digestion and phenol/chloroform extraction (both from Sigma, Poole, England), digested with 10 units of EcoRV and NotI (Life Technologies, Paisley, Scotland), run on a 1% agarose gel with appropriate size markers (Flowgen, Lichfield, England), Southern blotted onto nylon membrane (Amersham, Little Chalfont, England) and probed with $\alpha^{32}P$ labelled EGFP DNA (labelled using Megaprime, Amersham, Little Chalfont, England). EcoRV cuts within the virus backbone and NotI cuts within the recombination plasmid, revealing a band which is diagnostic of successful recombination. Virus stocks were grown up in roller bottles (Sigma, Poole, England), and were harvested from the extracellular fraction. Virus stocks were titrated by limiting dilution in OMK cells. The recombinant virus was designated HVSgp160/EGFPNeo.

Cells

Jurkat cells, a representative T-cell line, were grown in RPMI1640 medium supplemented with 5% FCS, 100 U/ml penicillin, 100 µg/ml streptomycin (all from Gibco, Paisley, Scotland). Cells were passaged by diluting 1 in 5 with fresh medium every third day. Cell culture was carried out in 75 cm³ Costar flasks (Sigma, Poole, England). Cells were incubated at 37° C. in the presence of 5% $CO_2$ in an air jacketed incubator (Sanyo Gallencamp PLC, Leicester, England).

Transduction protocol

Jurkat cells were infected using HVSgp160/EGFPNeo at a multiplicity of infection (MOI) of twenty using spinoculation. Spinoculation involved the mixing of virus and $2\times10^5$ cells in a total volume of 0.5 ml medium followed by centrifugation at 1,500 rpm for 90 min in a bench top centrifuge at room temperature. Spinoculation was carried out in 15 ml Corning tubes (Sigma, Poole, England). After spinoculation, cells were cultured in a volume of 2 ml of growth medium in 35×mm Corning culture dishes (Sigma, Poole, England). Cells were incubated at 37° C. in the presence of 5% $CO_2$ (Sanyo Gallencamp PLC, Leicester, England).

Fluorescent Microscopy and Flow Cytometry

Expression of HIV gp160 and EGFP as a fusion protein in the transduced cells was detected 48 h post-infection a) using a Zeiss Axiovert microscope and FITC filtered UV illumination and b) using an Epics XL/MCL flow cytometer (Coulter Electronics, Luton, UK). FCS/SSC electronic gates were set up, and dead cells were gated out on the basis of PI-positivity.

Results

FIGS. 1A and 1B shows, respectively, a field of infected Jurkat cells viewed under both phase contrast and blue light (i.e FITC filter) microscopy. A significant number of cells have been successfully transduced and exhibit the gp160/EGFP phenotype. Flow cytometric analysis revealed that 50% of the population expressed the EGFP fusion. Moreover, since the EGFP gene was cloned downstream of the gp160 gene, the latter was also expressed in the transduced T cells.

The data clearly demonstrate that the invention is capable of efficiently delivering the appropriate heterologous genes to the appropriate type of target cell (i.e T-cell or macrophage) in a stable manner. In addition the parental HVS used to construct the recombinant virus lacks the STP gene (ORF1), a preferred embodiment of the invention.

HVS Vector Development

It has been determined that although HVS recombinant viruses infect human T cells and persistence of viral DNA occurs long term, these cells do not produce infectious virus (11). In addition, in the natural host HVS exists in the latent form in T cells. However to minimise the risk of pathogenicity, disabled HVS viral vectors were produced that contain a replication-defective genome. The entire genome of HVS has been sequenced and 76 major open reading frames identified (29). For 60 of the predicted proteins homologous sequences with other herpesviruses are found, in particular with the human Epstein Barr virus (30). Although limited data are available for essential and non-essential genes in HSV-1 extensive analysis has been carried out on the genomes of human herpesviruses (31). Analogous genes present in HVS may have similar functions and therefore candidate genes exist for deletion.

However, initial deletions were made for genes present in HVS that do not have homologoues in other herpesviruses. As stated above the HVS 'parent' strain that was used is the non-oncogenic strain 11/S4 already deleted for the STP gene (ORF 01). Other candidate genes that may contribute to the transforming potential of HVS are ORF 14 (homologous to a MMTV LTR gene) and ORF 72 (cyclin D homologue). ORF 04 and ORF 15 were also deleted as these code for glycoproteins that have been found to be related to complement control proteins which down-regulate complement activity. These genes were sequentially deleted from the viral genome using homologous recombination. Transfer vectors were constructed containing sequences flanking the gene to be deleted. Viral DNA was produced from the 'parent' ORF 01-deleted virus and co-transfected with the appropriate transfer vector. Recombinant viruses were detected by PCR analysis of the DNA present in viral plaques. Virus DNA was then purified and co-transfected with another transfer vector to generate the next deletant. This procedure was repeated until all the genes listed above were deleted. As the terminal repeats of HVS genome are heterogeneous in size, this demonstrates that the virus is able to package DNA molecules which may be 20 kb shorter than the mean unit length (160 kb).

ORF06 Deletion

ORF06 (located between bp 12584 and 15967) encodes the major DNA binding protein. Thus deletion of this gene makes the virus replication deficient. To make a recombination cassette for deletion of ORF06 flanking DNA regions were excised from pSS54 which contains the region of HVS DNA from 11507 to 18013 (the KpnIF fragment). The KpnI (11507)-HaeII (12613) 1106 bp fragment 5' to the ORF06 coding region and the SpWI (15258)-BglIII (16407) 1149 bp fragment were excised and ligated together via synthetic oligomers. The oligomers also contain EcoRI and BamHI restriction sites, as shown below, to allow insertion of heterologous genes. It is necessary to maintain part of the 3' end of ORF06 as this contains the promoter for ORF07. The ligated KpnI-BglIII fragment was inserted into the pBluescript KS cloning vector to create the recombination cassette pMSL102.

Sequence of oligomers to link the fragments

```
   TGAATTCGGATCCGCATG (SEQ ID 1)

CGCGACTTAAGCCTAGGC (SEQ ID 2)
  HaeIII EcoRI   BamIII  SphI
```

ORF06 Construction to Generate Helper Cell Line

To produce HVS deleted for the ORF06 coding region, it is necessary to provide the ORF06 gene product in trans. This was achieved by producing a stable helper cell line. The ORF06 gene was excised from pSS54 as a HaeII (12613)-PstI (15998) fragment. Synthetic oligomers (as shown below) were used to precisely create the start of the coding region of ORF06 and to allow insertion into the expression vector pSVK3 (Pharmacia). Following ligation of the synthetic oligomers to the 5' end of the ORF06, the EcoRI-Psl fragment was ligated to pSVK3 to create pMSL103. This drives expression from the SV40 early promoter. Use of an alternative promoter minimises recombination events in the helper cell line.

Oligomer sequences

```
AATTCATGGCAACGAAGACAGCGCAACCTAGCGC (SEQ ID 3)

GTACCGTTGCTTCTGTCGCGTTGGAT (SEQ ID 4)
     EcoRI  ORF06 Start            HaeII
```

ORF51 Deletion

ORF51 encodes the potential receptor binding membrane protein of HVS. Therefore deletion of this gene renders the virus non-infectious. ORF51 is located between bp72626 and bp73432 of the HVS genome. To produce ORF51 flanking sequences for the recombination cassette, the BamHI (71692)-HpaI (72602) 910 bp fragment 5' to the ORF51 coding region and the Bst 11071 (73395)-PstI (73998) 601 bp fragment 3' to ORF51 were excised from pKK104 which contains the HVS EcoRI D fragment from 63020 to 77574, and ligated together via synthetic oligomers. These oligomers also contain EcoRI and BamHI restriction sites to enable insertion of heterologous genes and in addition the sequence required to maintain the polyA site for ORF52. Following ligation the BamHI-PstI fragment was ligated to the cloning vector pSP73 (Promega) to create the recombination cassette pMSL104.

Synthetic oligomer sequences

```
AACGAATTCGGATCCTTAATAATAATGAGCTGTA (SEQ ID 5)
TTGCTTAAGCCTAGGAATTATTATTACTCGACAT (SEQ ID 6)
  HpaI EcoRI  BamHI   ORF52 polyA    Bst11071
```

ORF51 Construction to Generate Helper Cell Line

The ORF51 gene was excised from pKK104 as a HpaI (72602)-StuI (73495) 806 bp fragment and cloned into the SV40 expression vector pSVK3. EcoRI linkers were ligated to the 5' and 3' ends of ORF51 to facilitate this cloning reaction. The resulting ORF51 expression vector was designated pMSL105.

ORF 57 Deletion

Orf 57 encodes a transcription activator with homology to HSV-1 UL54, an essential immediate early gene. To generate a virus containing a complete deletion of ORF 57, regions adjacent to the coding region of ORF57were amplified to allow homologous recombination with viral DNA. Primers have been designed; 5'-d GGC GAA TTC GTC TAT AAC TGA CTG GGT TGC TG (SEQ ID 7), 5'-d GCC CTG CAG GCA GTT ACT CAC CAT AGC TTG AG (SEQ ID 8), 5'-d GCC CTG CAG CAA GTG TCC AAG CTC TAC TTG TGC (SEQ ID 9), 5'-d GGG GCA TCC CTA TTG ATG TGC CAA GCA ATA GGG T (SEQ ID 10). These amplify two regions of HVS respectively; 77850 to 78260 bp and 79530 to 80120 bp. Suitable restriction sites have been incorporated into the primers to assist in cloning. A triple ligation was performed using these fragments and pUC18, previously digested with EcoRI and SphI, to derive pAW101. This plasmid was then linearised using PstI and ligated with the lacZ gene under the control of the hCMV IE promoter, to generate pAW102.

To generate a helper cell line, a fragment containing the coding region of ORF57 was amplified using PCR, and ligated with a T vector, pCRII, to derive pAW103. To generate a replication defective virus, ORF 06 was deleted, as above, as this is analogous to the Epstein Barr ALF2 gene which encodes the major DNA binding protein. It has been determined that EBV virus mutants in this gene, just as the alphaviruses studied to date, are unable to replicate. These replication deficient viruses were produced in a helper cell line providing the ORF 06 gene product in trans. The ORF 06 coding region was cloned into a eukaryotic expression vector containing the neomycin phosphotransferase gene. Following transfection of this vector into Vero cells a cloned helper cell line was produced using G418 selection. Monoclonal antibodies to this protein were provided by Dr R Randall (University of St. Andrews) which allowed us to characterise the ORF 06 deleted virus and helper cell line. Absence of the ORF 06 coding region in viruses produced from this cell line was confirmed by restriction analysis of viral DNA and replication deficiency confirmed by infecting Vero cells in a standard assay.

Production of Helper Cell Lines

The virus genes which are to be expressed in a stable cell line, in trans, are cloned in a suitable plasmid vector under control of their own, or heterologous 5' and 3' control sequences. This plasmid may also contain a selectable marker, eg the neomycin phosphotransferase gene which confers resistance of eukaryotic cells to the drug G418. Alternatively this gene may be provided on a separate plasmid, again under the control of heterologous eukaryotic control sequences, for instance the SV40 early promoter and appropriate polyadenylation signals. In all cases, cell lines are established thus. $5 \times 10^5$ cells (or sufficient to give 40–50% confluence) such as Vero or OMK are plated out onto 10 cm diameter tissue culture dishes in 10 ml of DMEM/10% foetal calf serum and incubated for 12–18 h at 37° C. in an humidified atmosphere containing 5% $CO_2$ in air. After this period 2 μg plasmid is transfected into the cells using DOTAP reagent as described elsewhere for transfection of virus DNA. This may be either a single plasmid which contains the appropriate gene and the selectable marker gene, or a mixture of 2 μg of each separate plasmid. Cells are then incubated at 37° C. in a humidified atmosphere containing 5% $CO_2$ in air for a further 48 hours. At this stage, the now confluent monolayers are detached from the plastic dish by removal of the medium, washing with 2×10 ml of phosphate buffered saline (PBS, Life Technologies Inc, Cat No. 20012) and treatment with 2 ml trypsin (0.25% w:v)/EDTA(0.2% w:v) solution in PBS. Fresh medium is then added to the cell suspension, the cells counted and then plated out into 96 well plates for cloning at limiting dilution or dispensed at 104 cells per 10 cm dish. The culture medium (DMEM/10% FCS) is supplemented with an appropriate concentration of G418 which is sufficient to cause 100% kill of non-transfected cells. The concentration is dependent both on cell passage number and cell type. A typical concentration for Vero cells at passage 150 is 800 μg/ml. Cells are then replaced in the previously described growth environment and observed at regular intervals for cell killing. Culture medium is replaced approximately every 3–4 days depending on cell death/growth rate. After 7–14 days individual clones of cells have grown and are then picked, grown to appropriate numbers and tested for the expression of the HVS gene transfected. This can be achieved through use of either immunofluoresence, Northern Blotting or RT-PCR, using methods well known in the art.

References

Rich. D P, L A Couture, L M Cardoza, V M Guiggo, D Armentano, P C Espino, K Hehir, M J Welsh, A E Smith, and R J Gregory (1993) *Hum Gene Ther.* 4: 461–476.

Gordon, E M and W F Anderson (1994) *Curr. Opinion Biotech.* 5: 611–616.

Smith, R L, A J Geller, K W Escudero and C L Wilcox. (1995) *J. Virol.* 69: 4593–4599.

Crystal, R G, N G McElvaney, M A Rosenfield, C Chu, A Mastrangeli, J G Hay, S L Brodyl, H A Jaffe, N T Eissa and C Danel (1994) *Nature Genet.* 8: 42–51.

Dai, Y, E M Schwarz, D Gu, W Zhang, N Sarvetnick and I M Verma (1995) *Proc. Natl. Acad. Sci. USA* 92: 1401–1405.

Varela-Echavarria, A, C M Prorock, Y Ron, and J P Dougherty (1993) *J. Virol.* 67: 6357–6364.

Locker, H and N Frenkel (1979) *J. Virol.* 29: 1065–1077.

Nahmias, A J, Lee F K annd S Beckman-Nahmias (1990) *Scand J. Infect. Dis.* 69: 19–36.

Fleckenstrin, B (1979) *Biochem. Biophys. Acta.* 560: 301–342.

Murthy, S C S, Trimble J J and R C Deroisers (1989) *J. Virol.* 63: 3307–3314.

Simmer, B, M Alt, I Buckreus, S Berthold, B Fleckenstein, E Platzer, and R Grassman (1991) *J. Gen Virol.* 72 1953–1958.

Berman, P W, T J Gregory, L Tiddle, G R Nakamura, M A Champe, J P Porter, F M Wurm, R D Hershberg, E K Cobb, and W Eichberg (1991) *Nature* 345: 622–625.

Griffiths, J C, E L Berrie, L N Holdsworth, J P Moore, S J Harris, J M Senior, S M Kingsman, A J Kingsman and S E Adams (1991) *J. Virol.* 65: 450–456.

Griffiths, J C, S J Harris, G T Layton, E L Berrie, T J French, N R Bums, S E Adams and A J Kingsman (1993) *L. Virol.* 67: 3191–3198.

Haigwood, N, P Nara, E Brooks, G Van Nest, G Ott, K Higgins, N Dunlop, C

Scandella, J Eichbeig and K Steimer (1992) *J. Virol.* 66: 172–182.

Wrin, T, T Loh, J Vennari, H Schuitemaker and J H Nunberg (1995) *J. Virol.* 69: 39–48.

Cao, Y, L Quin, L Zhang, J Safrit and D D Ho (1995) *N. Engl. J. Med.* 332: 201–208.

Moore, J P, Y Cao, L Qing, Q J Sattentau, J Pyati, R Koduri, J Robinson, C F Barbas, D R Burton, and D D Ho (1995) *J. Virol.* 69: 101–109.

Moore, J P and D D Ho (1993) *J. Virol.* 67: 863–875.

Sullivan, N, Y Sun, J Li, W Hofmann and J Sodroski (1995) *J. Virol.* 69: 4413–4422.

Clements, J C, R C Montelaro, M C Zink, A M Amedee, S Miller, A M Trichel, B Jagerski, D Hauer, L N Martin, R P Bohm and M Murphey-Corb (1995) *J. Virol* 69: 2737–2744.

Stevenson, M, C Meier, A M Mann, N Chapman, and A Wasiak (1988) *Cell* 53: 483–496.

Daniel, M D, H Rabin, H H Barahona ans L V Melendez (1972) *Proc. Soc. Exp. Biol. Med.* 136: 1192–1196.

Grassman R and B Fleckenstein (1989) *J. Virol.* 63: 1818–1821.

Chapman, B S, R M Thayer, K A Vincent and N L Haigwood (1991) *Nucleic Acids Res* 19: 3979–3986.

Pinter, A, W J Honnen, S A Tilley, C Bona, H1 Zaghouani, M K Gorny, and S Zolla-Pazner (1989) *J. Virol.* 63: 2674–2679.

Medveczky, M M, E Szomolanyi, R Hesselton, D DeGrand, P Geck, and P G Medveczky (1989) *J. Virol.* 63: 3601–3611.

Letvin, N L, M D Daniel, P K Sehgal, R C Desroisers, R D Hunt, L M Waldron, J J MacKey, D K Schmidt, L V Chalifoux, and N W King (1985) *Science* 230: 71–73.

Albrecht, J-C, J Nicholas, D Biller, K Cameron, B Biesenger, C Newman, S Witmann, M A Craxton, H Coleman, B Fleckenstein, and R W Honess (1992) *J. Virol* 66: 5047–5058.

Gompels, U A, M A Craxton and R W Honess (1988) *J. Virol.* 62: 757–767. Roizman, B, Whitley, R J and C Lopez (1993) *The Human Herpesviruses*, Raven Press.

What is claimed is:

1. A herpesvirus saimiri (HVS) vector which has inserted therein at least a part of a nucleotide sequence encoding an envelope protein of human immunodeficiency virus (HIV), wherein said HVS vector lacks or has a mutation in its STP gene (ORF1) such that the gene product is lacking or is non-functional.

2. A vector according to claim 1 wherein the nucleotide sequence encoding an envelope protein of HIV is from a primary isolate of HIV.

3. A vector according to claim 1 which further includes deletion of at least one non-essential gene.

4. A vector according to claim 1 which has been further modified so that a gene encoding a transcriptional control protein is mutated and/or deleted so as to disable the replication cycle of the virus.

5. A vector according to claim 1 which has been further modified so that a gene encoding a glycoprotein is mutated and/or disabled and/or deleted so as to down-regulate inhibition of complement activity.

6. A vector according to claim 5 wherein the gene to be mutated and/or disabled and/or deleted is either ORF4 and/or ORF15.

7. An isolated A target cell including the vector of claim 1.

8. An isolated A target cell including the vector of claim 2.

9. An isolated A transduced cell infected by the vector according to claim 1.

10. An isolated A transduced cell infected by the vector according to claim 2.

11. An immunogenic composition comprising the vector according to claim 1 in addition to a suitable excipient or carrier.

12. An immunogenic composition comprising the vector according to claim 2 in addition to a suitable excipient or carrier.

13. An immunogenic composition according to claim 11 wherein the immunogenic composition is in the form of a fluid which is adapted for injection intravenously, intramuscularly or subcutaneously into an individual.

14. An immunogenic composition according to claim 11 wherein the immunogenic composition is in the form of a fluid which is adapted for use as an aerosol whereby droplets of the immunogenic composition can be delivered to the respiratory tract.

15. A composition comprising a herpesvirus saimiri vector (HVS) which has inserted therein at least part of a nucleotide sequence encoding an envelope protein of HIV, wherein said HVS vector lacks or has a mutation in its STP gene (ORF1) such that the gene product is lacking or is non-functional.

16. A composition according to claim 15 wherein the nucleotide sequence encoding an envelope protein of HIV is from a primary isolate of HIV.

* * * * *

UNITED STATES PATENT AND TRADEMARK OFFICE
CERTIFICATE OF CORRECTION

PATENT NO. : 6,692,955 B1
DATED : February 17, 2004
INVENTOR(S) : Meredith et al.

Page 1 of 1

It is certified that error appears in the above-identified patent and that said Letters Patent is hereby corrected as shown below:

<u>Title page,</u>
Item [30], Foreign Application Priority Data, should read
-- Nov. 28, 1998  (GB) 9826069.8 --

<u>Column 16,</u>
Lines 52-59, should read
-- 7. An isolated target cell including the vector of claim 1.
   8. An isolated target cell including the vector of claim 2.
   9. An isolated tranduced cell infected by the vector according to claim 1.
  10. An isolated tranduced cell infected by the vector according to claim 2. --

Signed and Sealed this

Eighteenth Day of May, 2004

JON W. DUDAS
*Acting Director of the United States Patent and Trademark Office*